United States Patent
Choi et al.

(10) Patent No.: US 11,992,319 B2
(45) Date of Patent: May 28, 2024

(54) METHOD OF MAKING A NEURAL INTERFACE SYSTEM

(71) Applicant: The Board of Regents of The University of Texas System, Austin, TX (US)

(72) Inventors: Paul Yoonsu Choi, Edinburg, TX (US); Bong Kyun Kim, Edinburg, TX (US); Bernardo Garza, Mission, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1048 days.

(21) Appl. No.: 16/664,329

(22) Filed: Oct. 25, 2019

(65) Prior Publication Data

US 2020/0054229 A1    Feb. 20, 2020

Related U.S. Application Data

(62) Division of application No. 15/523,534, filed as application No. PCT/US2015/058013 on Oct. 29, 2015, now abandoned.

(Continued)

(51) Int. Cl.
*A61B 5/24*    (2021.01)
*A61B 5/00*    (2006.01)
(Continued)

(52) U.S. Cl.
CPC .............. *A61B 5/24* (2021.01); *A61B 5/6877* (2013.01); *A61F 2/72* (2013.01); *A61N 1/0551* (2013.01);
(Continued)

(58) Field of Classification Search
CPC .............. A61B 5/24; A61B 2562/0209; A61B 2562/12; A61N 1/0551; H01B 17/60
See application file for complete search history.

(56) References Cited

U.S. PATENT DOCUMENTS 6,829,498 B2    12/2004    Kipke et al.
7,058,455 B2    6/2006    Huie, Jr. et al.
(Continued)

FOREIGN PATENT DOCUMENTS

CN    103055985 A  *  4/2013
WO    WO-2012139124 A1  *  10/2012  ......... A61B 5/04001

OTHER PUBLICATIONS

Kameswaran et al. "A novel neuroprosthetic interface with the peripheral nervous system using artificially engineered axonal tracts." Neurological Research, 2008, vol. 30, 1063-1067.

(Continued)

*Primary Examiner* — Peter Dungba Vo
*Assistant Examiner* — Jose K Abraham
(74) *Attorney, Agent, or Firm* — Kowert, Hood, Munyon, Rankin & Goetzel, P.C.; Gareth M. Sampson

(57) ABSTRACT

Neural interfaces with the peripheral nervous system have been developed to provide a direct communication pathway between peripheral nerves and prosthetic limbs. Described herein is a method of making a microchannel integrated neural interface device comprising a plurality of hollow cylindrical electrodes in a PDMS scaffold, which can control the reinnervated muscles and interpret neurological signals. The acquired bioelectrical signals can be used for the interpretation of mind and create a neural map.

8 Claims, 11 Drawing Sheets

Related U.S. Application Data

(60) Provisional application No. 62/073,307, filed on Oct. 31, 2014.

(51) Int. Cl.
    *A61F 2/72*     (2006.01)
    *A61N 1/05*     (2006.01)
    *H01B 17/60*     (2006.01)

(52) U.S. Cl.
    CPC ...... *H01B 17/60* (2013.01); *A61B 2562/0209* (2013.01); *A61B 2562/028* (2013.01); *A61B 2562/12* (2013.01)

(56) References Cited

U.S. PATENT DOCUMENTS

| | | | |
|---|---|---|---|
| 8,447,392 B2* | 5/2013 | Llinas | A61B 5/24 600/377 |
| 8,666,499 B2* | 3/2014 | Youn | A61N 1/37288 607/116 |
| 8,676,334 B2 | 3/2014 | Youn et al. | |
| 9,433,787 B2* | 9/2016 | Elias | A61B 5/685 |
| 2005/0016657 A1* | 1/2005 | Bluger | A61N 1/05 156/50 |
| 2005/0107858 A1* | 5/2005 | Bluger | A61N 1/05 607/115 |
| 2008/0140153 A1* | 6/2008 | Burdulis | A61N 1/0551 607/46 |
| 2010/0041972 A1* | 2/2010 | Mason | A61B 5/685 607/148 |
| 2010/0211172 A1 | 8/2010 | Bellamkonda et al. | |
| 2011/0016710 A1* | 1/2011 | Dadd | A61N 1/0541 29/874 |
| 2011/0021943 A1* | 1/2011 | Lacour | A61N 1/0551 607/118 |
| 2012/0253423 A1 | 10/2012 | Youn et al. | |
| 2013/0303873 A1* | 11/2013 | Voros | H05K 1/0283 604/20 |
| 2013/0333918 A1* | 12/2013 | Lotfi | B23K 26/364 174/121 R |

OTHER PUBLICATIONS

Seifert et al. "Normal Molecular Repair Mechanisms in Regenerative Peripheral Nerve Interfaces Allow Recording of Early Spike Activity Despite Immature Myelination" IEEE Transactions on Neural Systems and Rehabilitation Engineering, vol. 20, No. 2, Mar. 2012.

International Search Report and Written Opinion for PCT Application No. PCT/US2015/058013, dated Jan. 11, 2016.

International Preliminary Report on Patentability for PCT Application No. PCT/US2015/058013, dated Jan. 11, 2016.

Hoffmann et al. "New Technologies in Manufacturing of Different Implantable Microelectrodes as an Interface to the Peripheral Nervous System" BIOROB, 414-419 (2006).

Office Action for U.S. Appl. No. 15/523,534 dated Oct. 30, 2018.

Final Office Action for U.S. Appl. No. 15/523,534 dated Jul. 1, 2019.

\* cited by examiner

METHOD OF MAKING A NEURAL INTERFACE SYSTEM

PRIORITY CLAIM

This application is a divisional application of U.S. patent application Ser. No. 15/523,534, filed May 1, 2017, which is a 371 of PCT Application PCT/US2015/058013, filed Oct. 29, 2015, which claims priority to U.S. Provisional Application Ser. No. 62/073,307 entitled "Microchannel Scaffolds and Microtube Electrodes for a Neural Interface System" filed Oct. 31, 2014, which is incorporated herein by reference in its entirety.

BACKGROUND OF THE INVENTION

1. Field of the Invention

The invention generally relates to neural interfaces for the peripheral nervous system.

2. Description of the Relevant Art 86 billion neurons in our brain manage and sustain our daily life; however the specific functionality of individual brain neurons is still very much a mystery. Although cultured neuronal networks have shown a variety of mechanism of neuronal functionality, individual neuron interfaces have not yet been introduced during in vivo animal studies. State-of-the art electrophysiological techniques can only access a group of neurons, and this makes modality specific applications difficult, because there is no way to specifically interact with a neuron within a group responsible for efferent or afferent signals. Neuronal interface signals captured from awake-freely behaving animals would be an important tool for the next level of clinical applications. Although it is possible to compile details of cellular or even subcellular information from deceased animal brains, such a database would hardly provide the necessary behavioral or cognitive information.

If a nerve is damaged, for example if a nerve is cut, crushed, or stretched, signals between the brain and the portion of the body effected by the damaged nerve are disrupted. Damage to nerves can be caused by diseases (e.g., arteriosclerosis, diabetes, Buerger disease) or traumatic injuries (e.g., car accidents, sports injuries, industrial accidents, etc.). The number of disabled persons suffering from congenital or acquired nerve damage is increasing every year, and the rehabilitation and return to the normal social life for these disabled persons is highly desirable.

Persons who have suffered the loss of an extremity (e.g., a hand, a portion of their arm or a portion of a leg) rehabilitate by wearing a prosthetic device (e.g., a prosthetic hand, a prosthetic leg, prosthetic arm, etc.). An ideal limb prosthesis is one that the patient can naturally wear and control, i.e. one that is directly interfaced with the patient's peripheral nerve stump. While robotic technology is advanced enough to produce highly sophisticated prosthetic devices, the technology of interfacing peripheral nerves to electronic prosthetic control systems is less than ideal.

Alternatively, when a patient suffers damage to a nerve, with the limb remaining in place, the nerve may be surgically repaired and the axons will regenerate into the damaged limb, but are not necessarily guided back to the correct muscle or sensory structure.

Neural interface technologies are envisioned to facilitate direct connections between the nervous system and external technologies such as limb prosthetics or data acquisition systems for further processing. In amputees, such technologies can provide direct neural control of prosthetic movements and restore sensory feedback by functionally reconnecting damaged efferent motor and afferent sensory pathways. The peripheral nerve has been one target for bidirectional interfacing, with renewed interest generated by reports that peripheral nerve tissue is viable for interfacing even years after injury or amputation. Several designs, such as cuff electrodes, flat interface nerve electrodes (FINE), longitudinal intrafascicular electrodes (LIFE), Utah Slanted Electrode Arrays (USEA), and regenerative sieve and microchannel electrodes demonstrated selective recording and stimulation. However, these devices have limited electrode sites and recordings can only be obtained from a limited number of nerve fascicles.

A neural interface placed to record signals from the regenerated axons can provide information that can be used to control limb movement (in either a prosthetic device or an existing reattached limb. The key factor in determining how much information can be extracted from a neural interface is the number of functioning and independent electrical connections it makes with axons in the nerve to which it is applied. The more contacts that can be made, the more successful the patient will be in controlling the effected limb.

SUMMARY OF THE INVENTION

In an embodiment, a microchannel integrated neural network device includes: a body; a plurality of microchannels formed in the body, wherein the microchannels have an internal diameter approximately equal to the diameter of a nerve axon; and one or more electrodes, each electrode disposed in a portion of one of the microchannels. The body is formed from a biologically inert polymer. The microchannels may have an internal diameter of between about 5 micrometers to about 200 micrometers. Each electrode may be a tubular electrode oriented coaxially with the longitudinal axis of the microchannels. Electrodes are formed from a conductive, biologically inert metal (e.g., gold).

In an embodiment, the device includes one or more wires coupled to the electrodes, wherein the wires allow communication between the electrodes and an electronic signal detection device.

In a specific embodiment of the device, the device includes: a non-conductive biologically inert support; a polymeric layer disposed on the surface of the support, wherein the microchannels are formed in the polymeric layer; and one or more electrodes, each electrode disposed in a portion of one of the microchannels; and a plurality of conductive metal lines formed on the substrates. Each conductive metal line includes: a contact pad which is configured to couple the conductive metal line to an external signal measuring device; and contact regions which couple the conductive metal line to one or more to the electrodes. The non-conductive biologically inert support, in one embodiment, is a silicon wafer.

In an embodiment, a method of making the microchannel neural interface device includes: placing a plurality of metal wires in a curable composition, wherein the curable composition comprises a polymerizable compound and wherein the metal wires have a diameter approximately equal to the diameter of a nerve axon; curing the curable composition to form a polymeric object having a plurality of metal wires embedded in the polymeric object; removing the metal wires from the polymeric object to form a plurality of microchannels within the polymeric object; and coupling electrodes to one or more of the microchannels. In some embodiment, the metal wires are copper wires. In some embodiments, the curable composition comprises a curable monomer. In a specific embodiment, the curable monomer is a monomer capable of being polymerized into polydimethylsiloxane. In an embodiment, removing the metal wires comprises dissolving the metal wires.

In an embodiment, a neural interface system comprising a plurality of microchannel integrated neural network devices and an electronic controller coupled to each of the microchannel neural interface devices, wherein the electronic controller receives bioelectrical signals from peripheral nerves coupled to the microchannel neural interface devices.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
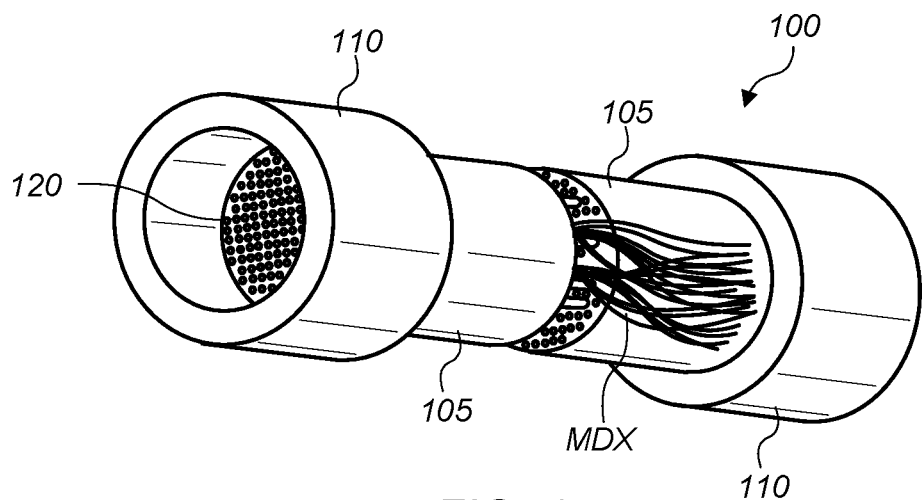
FIG. 1 depicts a perspective view of an exemplary microchannel integrated neural network (INN) device.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

Neural interface technologies are envisioned to facilitate direct connections between the nervous system and external technologies such as limb prosthetics. In amputees, such technologies can provide direct neural control of prosthetic movements and restore sensory feedback by functionally reconnecting damaged efferent motor and afferent sensory pathways. The peripheral nerve is an ideal choice for bidirectional interfacing based on the knowledge that peripheral neural tissue is viable for interfacing even years after injury or amputation. Interfacing directly with peripheral nerves has the advantage of minimizing surgical risk and complications associated with cortical implants and avoiding the reactive gliosis and electrode failure which plagues cortical interface designs due to tethering forces and mechanical damage.

In order to access peripheral nerves, a peripheral neuron interface is used. Contemporary electrophysiological devices can typically only access a group of neurons whether they are in a brain cortex or in a peripheral nerve. Implantable electrodes, even with a 10 µm cell size, tend to receive neural signals from neighboring neurons leading to cross talk and unreliable performance.

In one embodiment, a microchannel neural interface provides a neural interface with the peripheral nervous system. The microchannel neural interface provides a direct communication pathway between peripheral nerves and external devices. The microchannel neural interface uses regenerated peripheral nerves to control the reinnervated muscles and/or interpret neurological signals matching specific behavior patterns. The subject's bioelectrical signals can be mapped from specific peripheral nerves.

Figure 2:
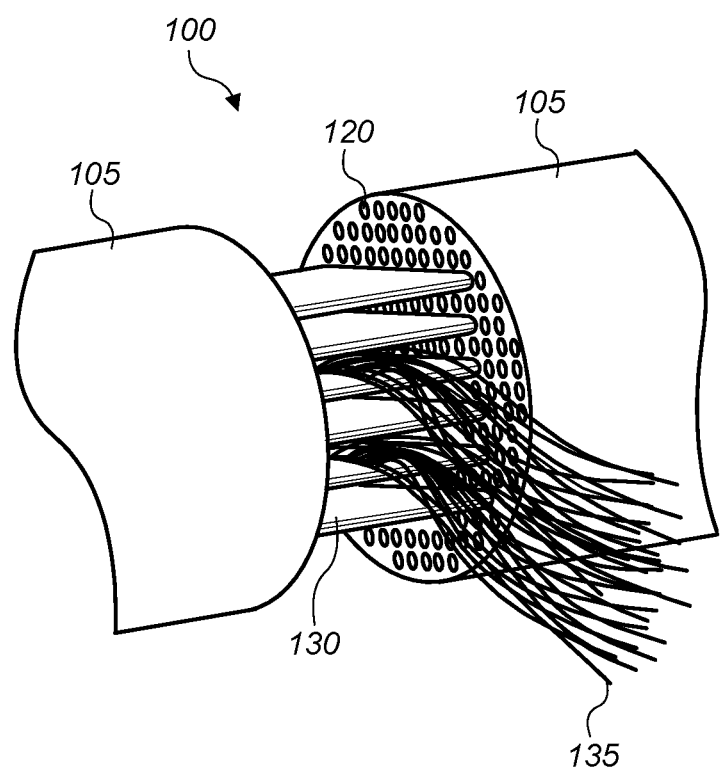
FIG. 2 depicts a close up view of the electronic controller interface wires extending out of the INN device.
Figure 8:
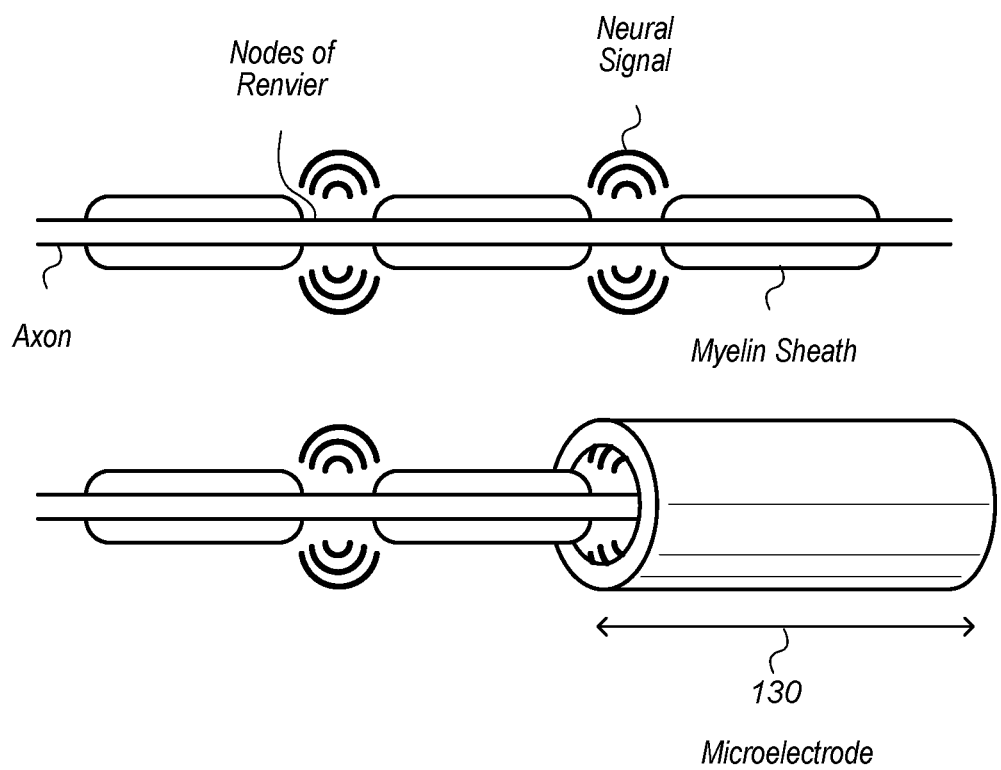
FIG. 8 shows how the gold microtube electrodes are long enough to cover and record neural signals from the single source of the axon with high selectivity.

A microchannel integrated neural network ("INN") device comprises a plurality of microchannels, each of the microchannels having a diameter approximately equal to the diameter of a single peripheral nervous system axon in the damaged region. The INN also includes a plurality of electrodes coupled to each of the microchannels. The electrodes serve as an interface between the peripheral nerve axons and an electronic controller. The electronic controller can be used to electrically monitor the activity of the peripheral nerves and/or couple the peripheral nerves to a prosthetic device. A perspective view of an exemplary INN device 100 is shown in FIG. 1. FIG. 2 depicts a close up view of the electronic controller interface wires 135 extending out of INN device 100. The INN device includes a body 100 having two opposing collars 110. Collars 110 have a diameter sufficient to receive the ends of a severed nerve. A plurality of microchannels 120 extend through body 105 of the INN device forming a path through which individual axons can extend. A plurality of electrode wires 135 are coupled to microelectrodes 130. FIG. 8 shows how the microelectrodes are, in some embodiments, long enough to cover and record neural signals from the single source of the axon with high selectivity.

Regenerating peripheral nerve axons grow into individual microchannels and can be naturally selected as an individual neuron communication unit by microchannel size control. In one embodiment, the microchannels have a diameter approximately equal to the diameter of an axon. Peripheral nerve axons generally have a diameter of between about 5 micrometer and 200 micrometers. The length of the microchannel neural interface device can range from 5 mm up to 100 mm (or more) in length. The microchannels are thus configured so that only one axon can occupy one microchannel due to space limitations, for example, by limiting the diameter of the microchannels to the diameter of the axons (e.g., between 1 micrometer and 200 micrometers). Other axons will thereby be forced to enter other channels. Each of the microchannels can be isolated individually for neuronal communication and build up neuronal networks which can be controlled by individual microchannel communication units.

The INN can have immediate response time and its circuitry can be configured to create a massive neuronal network. The size of the neuronal network depends solely on the supply of electronic chips and acquisition systems. When using the peripheral nervous system, the access points are 43 pairs of peripheral nerves. The total 86 peripheral nerves have two sensory and motor branches making 172 access points. Each INN can be designed with 512 microchannels which is the commercially available channel number. If we would incorporate microelectrodes with all microchannels, we could have 88,000 individual neuron connections which would make sophisticated neuronal networks in the brain. The peripheral nerve access points will follow all of the peripheral nerve branches from the whole spinal cord and will have enough space when compared to intracortical electrodes or EcoG electrodes. This individual nerve branch access will make the initial target of two thousand individual neuron interfaces to the brain a very realistic approach. It will be composed of two peripheral nerve branches; each has 1024 channels including both sensory and motor nerves. Peripheral nerve neurons are connected to the brain neurons through additional spinal cord neurons as shown in the FIG. 3. The synaptic connections of the neural networks allow for an individual brain neuron interface using an innovative regenerative peripheral nerve interface which is non-invasive to brain. The brain neuron activation will be synchronized by the individual peripheral nerve neuron activation.

In one embodiment, an INN is made by inserting a plurality of metal wires (e.g., copper) into a polymeric tube. The metal wires are secured within the tube by curing a polymeric solution to form a polymeric object having metal wires embedded in the polymer. The metal wires are removed from the polymeric object by dissolution of the metal using solution chemistry. The resulting polymeric object includes a plurality of microchannels formed in a polymer.

Electrodes are formed by plating metal wires (e.g. copper) with gold. The gold coated metal wire is selectively etched to dissolve the metal wire, while leaving the gold coating. The resulting gold electrode is coupled to a wire (e.g., a copper wire) and positioned in the microchannels. Since the resulting electrode is in a hollow cylindrical form, the regenerating nerve can growth through the electrode as it grows within the microchannel. Thus, the nerve is in contained within the electrode, allowing individualized monitoring of the signals passing through the nerve while minimizing cross-talk and other electrochemical signals that would make monitoring an individual nerve difficult. While the use of gold is preferred, it should be understood that any conductive metal can be used to form the electrodes.

In one embodiment, the first step in fabricating the INN device is preparing the micro wires. It is necessary to spool the wires around a wheel or similar circular object. Each lap produces one channel of micro wire and it is optimal to fit as many wires as possible into the polymeric (e.g., polysulfone) tube. Also, cut 5-10% of the wires to be double the necessary length. Align and tie them to the shorter bundle. The wires that are double the length will be referred to as the longer wires (they are all one bundle). The longer wires facilitate in preparing the device, but will be discarded after the process. Next, cut the shorter wires at a diagonal angle to make it easier to insert them into a polysulfone tube.

In order to insert the wire into the polysulfone tube, twist the shorter wires around the longer wires to keep the shorter wires from spreading out. Then apply as small amount of super glue as possible to the cross section of the shorter wires to make all wires stick together securely. Once the glue has dried, cut the polysulfone tube to the desired length and pull the longer wires through the polysulfone tube until the shorter wires fit inside. The polysulfone tube should be able to slide up and down the wire without too much resistance.

Solder the end (where there are more wires) of the wires to a metal object. It will be used to maximize heat transfer into the wires in the tube when placed in an oven. Mix polydimethylsiloxane ("PDMS") base with PDMS curing agent at a 10 to 1 ratio, respectively. Stir and mix with a stirring rod for 20 minutes. Put the PDMS solution into a vacuum chamber until all air bubbles dissipate. Then remove the PDMS solution from the chamber. Next, position the polysulfone tube so that only the longer wires are inside it. Then place everything except the metal object into a test tube vertically and fill it with the PDMS solution. Each wire must be soaked thoroughly. Make sure each wire is completely straight and they do not tie onto one another. Place tape or aluminum around the base of the test tube to stabilize it. Now, place the tube into the vacuum chamber until all air bubbles dissipate.

Put the tubes in an aluminum boat. Fill the boat so that it is completely submerged with PDMS solution to make sure the channels are filled thoroughly. Put the boat in the vacuum chamber until all air bubbles disappear. Then, while the polysulfone tube and wires are still in the boat and the solution, slowly and carefully pull the wires so that the polysulfone tube covers the part with higher concentration of wires. Next, take it out of the boat and place it on a plate, cover it with a metal object and put it into an oven at 90° C. for two hours. This will make the PDMS solution solidify.

Cut off all the polysulfone tube to leave only the wires and the hardened solution. Cut off the longer wires that were used only to assist in pulling the wires into and out of the polysulfone tube. Cut a small piece of the micro tube and cover it completely with hot glue from a glue gun. Let it dry and then cut to desired length with a sharp blade or knife. Place under a microscope and remove the glue.

Put the tube into a copper etching solution and leave overnight. This will remove copper wires entirely leaving behind the finished PDMS scaffold. Nerve regeneration will take place through the channels of the scaffold.

Microtube electrodes may be formed by the following process. Cut a piece of copper wire and remove the insulation from both ends (1 cm). Connect one end of the wire to the negative end of a power supply. Connect the positive end of the power supply to a small metal fence. Fill a beaker with gold solution and place the metal fence and the end of the wire opposite the negative terminal into it. Make sure they do not touch. Apply 2 volts to the terminals and leave for two hours. Afterwards, the end of the wire that was in the solution will be covered with gold. Cut the gold covered parts to desired length. Put the parts into copper etching solution overnight. The next day, filter the solution to separate the gold electrodes from the solution. Take a thin copper wire and super glue with as little glue as possible to the gold electrode. This electrode will be used to harness electrical signals from the body.

Position the gold electrodes in the microchannels of the PDMS scaffold. The electrodes should be placed such that the hollow part of the electrode is coaxial with the microchannel, allowing regenerating nerve tissue to grow through the electrode as it grows along the microchannel.

Figure 21:
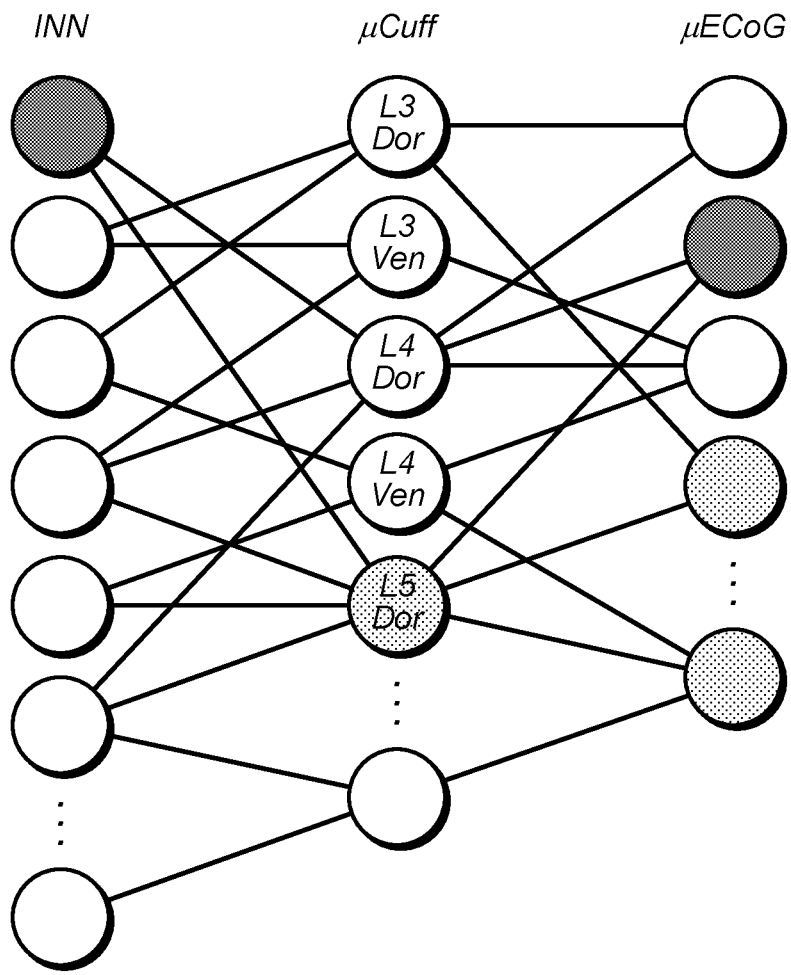
FIG. 21 depicts an exemplary node map.

Since our brains sustain 86 billion densely packed neurons, there is not enough space for implantable electrodes without damaging brain tissue and therefore sacrificing normal brain function. Even if we could place electrodes for single neuron communication, the morphology near the electrodes would already be changed and could not give the original biological information of the brain. The INN has a bypass signal pathway to the brain and keeps the brain intact. The individual neuron communication with the brain will be achieved by the three-level hierarchical network of microchannel neural interface systems. The individual axon communication with an integrated neural network (INN) interface system, the sensory and motor modular communication with a micro cuff electrode array (µCuff) and a the topographic group response with the microelectrocorticography array (µECoG) are all incorporated as a single neural network. This three-level neural signal network patterns can be decoded, since the signal source will be identified from the starting point and it is the least complicated one axon signal. It will be similar to a TV screen which has RGB color pixels. In a TV screen each pixel is compiled as a group and finally projected as the image. In comparison, we can capture the three-level neural network responses to a single neuron activation therefore making µECoG based brain mapping possible. The correlation of the signals received in each of the INN, µCuff, and µECoG to the animal's behavioral patterns can be used to specifically describe the signals of the three-level neural network patterns. The total analysis with all possible single axon stimulation will produce an image of mapped behavior to the brain. As the pixels in the TV screen correspond to the x-y location information, our single neuron microtube electrodes have the designated nerve information corresponding to the axons fired through the INN and then µCuff and µECoG. Contemporary bioinformatic techniques can capture sophisticated electrophysiological signals from large numbers of neurons. Electro physiological analysis of the three-cell network can be generated as a node map, as shown in FIG. 21. In the node map the exemplary signal sensed in the INN maps to the L4 and L5 dorsal roots (µCuff level) which corresponds to a specific µECoG pattern from the brain.

The unprecedented capability of the INN is not only for large-scale recording and modulation but also for the individual exclusive neuron communication. Individual neuron stimulation will generate a INN base map (coded as, $X_{INN}=\mu_{Cuff}=Z_{\mu ECoG}$) designated to a specific neuron, which is similar to DNA base pairs (bps). All base maps generated by individual neuron stimulation will be the building blocks of the Neuroma. Complex higher level maps of the INN can be developed from multiple neuron stimulations; these maps can be exponentially increased in complexity with the increase of stimulation sites due to the massive synaptic connection. The overall complexity of INN mapping with multiple neuron stimulations would be expected to be similar to the complexity of mapping genes within the genome. The base maps of the INN may be used to decipher the higher level INN maps similarly to the way sequences of nucleobases are used to decipher a gene expression. Specific behavioral patterns are related to certain specific multiple neuron activations, and will be used to develop higher lever maps of INN which will be identified by the combination of base maps. It will be an innovative and fundamental tool which can describe behavioral patterns in freely behaving animals in direct relation to specific neuron activity. The unique combination of multiple base map expressions developed will become an exclusive neural signal complex determined for a specific behavioral pattern. It is similar to how specific genes can be identified by DNA sequencing with a particular length of base pairs. One substantial difference between the development of the Genome and the Neurome is that the Neurome requires the study of awake, freely behaving animals, unlike the Genome that was discovered using blood samples without the complication of maintaining live subjects, which has hampered any practical progress of the development of the Neurome to date. The single neuron network of the INN makes it possible to develop the Neurome with the base map, becoming its fundamental unit. Unlike the Genome, in which each gene can be expressed by four nucleobases in a long line of sequence, the Neurome will be developed by describing a specific temporal behavior using the combination of base map identification and a serial base map combination for a specific period of a behavioral pattern.

As discussed above, the INN includes two parts: microchannel scaffold and microtube electrodes. The microchannel scaffold divides the regenerated nerves into specific groups of neurons, which can be tuned down to single axon regeneration in a microchannel. Neural recording and stimulation signals are forced to flow longitudinally within the microtube electrodes embedded in the microchannel scaffold which makes each microchannel independent from every other microchannel, making it possible retrieving specific signals. The incorporation of microchannel scaffold and microtube electrode will address one of the ultimate goals in neuroscience research: the single neuron interface.

The intermediate nodes of the three-level neural network are composed of µCuffs which will be placed on the spinal ventral roots or dorsal roots. The spinal roots are physically separated as motor or sensory axons which give an important advantage for the INN neural interface design. The nerve branches of the PNS have mixed with somatosensory and motor axons to have the closed loop for behavioral activity and responses. Only the nerve branch of the spinal nerve roots is accessible to the separated sensory and motor branches. The µCuff will access the ventral and dorsal roots outside vertebra and distal to the dorsal root ganglion.

µECoGs with 32 microwires were developed for the top level brain communication. The specific patterns of µECoG will be correlated to a unique stimulation combination of the single neuron peripheral nerve interfaces. One µECoG array can be used to cover both the primary and secondary somatosensory cortex (SI and SII). Another µECoG is placed on the primary motor cortex by the somatosensory region. The density of µECoG electrodes can be varied up to at least 200 electrodes. A high resolution brain mapping using a combination of INN, µCuff, and µECoG can be achieved.

The INN has significant potential as neuroscience research test beds, if they are combined with biochemical neurotropic factors. The layer by layer structure of the INN can be coated with different neurotropic factors on each layers to separate the growth of sensory or motor specific axons into individual layer and its microchannels. Multiple layers will encapsulate multiple neurotropic factors, such as nerve growth factor (NGF), neurotrophin-3 (NT-3), brain-derived neurotrophic factor (BDNF), and neurotrophin 4/5 (NT-4/5), ciliary neurotrophic factor (CNTF), and glial cell line-derived neurotrophic factor (GDNF). These combined biochemical test beds will have unique benefits of not only analyzing multiple neurotrophic factors at a time but also keeping the same biological conditions at the cellular level for all neurotropic factors. Inducing the specific axonal growth from a single tube structure to biochemically infused microchannels could provide data for a more in-depth analysis of axon growth behavior.

In an embodiment, an animal model of neural interfaces and a method useful for evaluating strategies to communicate with individual neurons in the peripheral nervous system and which will be traced up to the individual neurons in the brain can be created using microchannel neural interfaces. This animal model has been designed for use in any type of electrophysiological or brain disease research.

INNs can be used to develop a general electrophysiological animal model covering all of the peripheral nervous system and almost all motor and sensory cortex including the primary motor cortex, supplementary motor cortex, posterior parietal cortex, premotor cortex, and somatosensory cortex. Since we are using the peripheral nervous system, the access points are pairs of spinal peripheral nerves (12 cranial peripheral nerves can be added with delicate surgery). In total, 62 peripheral nerves have two sensory and motor branches making 124 access points. Each INN can be placed on an access point and designed to support 512 microtube electrodes which is the commercially available interface number. If necessary, 2,000 microtube electrodes can be designed in a microchannel neural interface. If incorporating the 2,000-electrode INN with all sensory and motor roots on a spinal cord, there would be 248,000 individual neuron connections which could be utilized to make a very sophisticated neuronal network in CNS-PNS. A network such as this would give great insight into the vast communication pathway between the CNS and the PNS.

Figure 3:
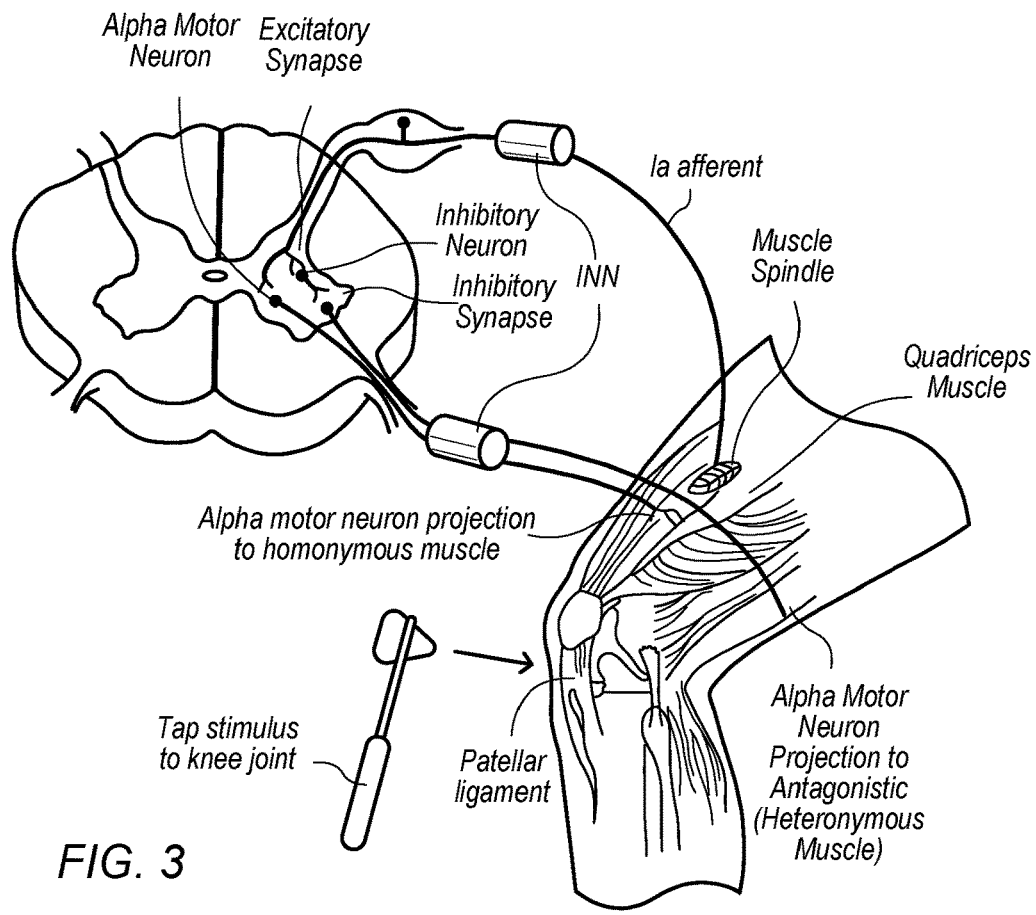
FIG. 3 depicts a schematic diagram of peripheral nerve neurons connected to the brain neurons through additional spinal cord neurons.
Figure 4:
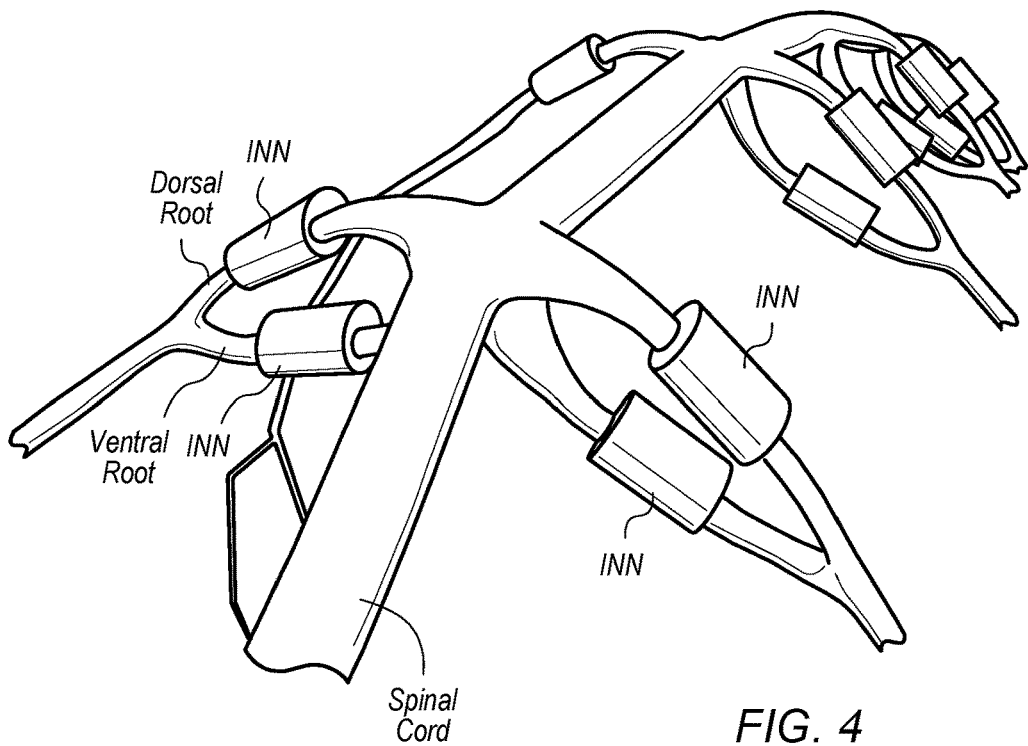
FIG. 4 depicts a perspective view of implanted INN devices.

The INN is composed of both the microchannel scaffolds and the microtube electrodes. Along with the unprecedented single neuron interfaces, the microchannel neural interface has separated the sensory and motor communication and transfers data separately through different signal pathways. FIG. 3 is a schematic diagram of microchannel neural interfaces implanted in the dorsal and ventral roots of the spinal cord. One INN is coupled to the sensory nerves and the other is coupled to the motor nerves. With this natural selection, the INN responsible for the motor signals would be implanted in the ventral root, and the INN responsible for the sensory signals would be implanted in the dorsal root. FIG. 4 shows the implanted INNs in an animation view.

Figure 5:
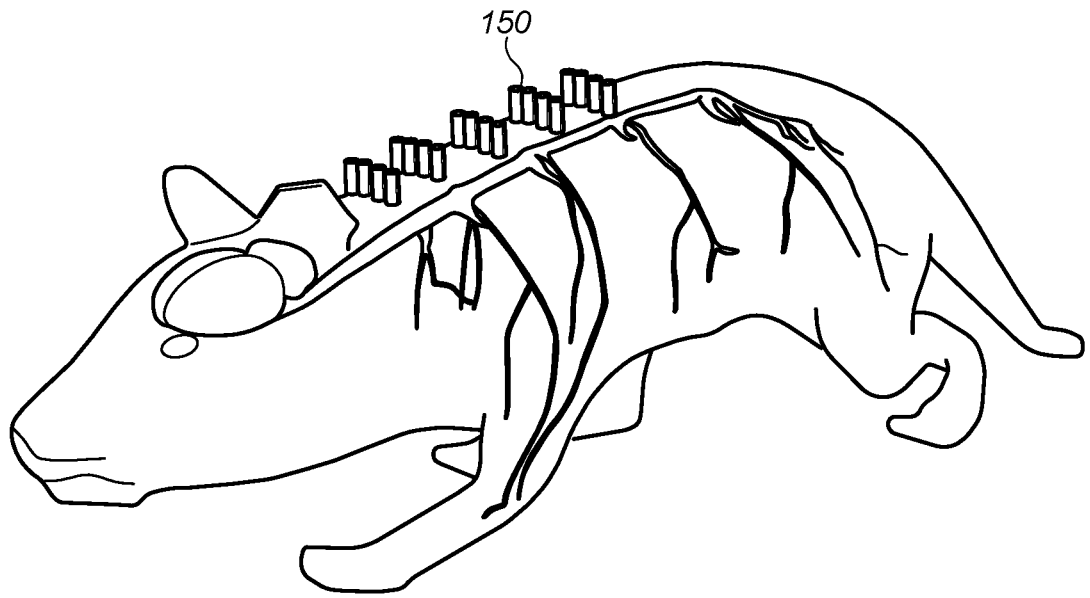
FIG. 5 depicts a schematic diagram of a neural interface system coupled to an animal.

Out of 31 pairs of spinal peripheral nerves, 5 pairs are selected as one type of animal model shown in FIG. 5. There are ten branches making a total of twenty INNs on sensory or motor roots (not shown). Each INN is connected to one socket 150 on the back which has 512 electrical connections (2,000 connections are possible using microtube electrodes). There are currently 512 electrical channels commercially available for data acquisition which is still challenging because of the huge volume of recorded data.

Figures 6A, 6B:
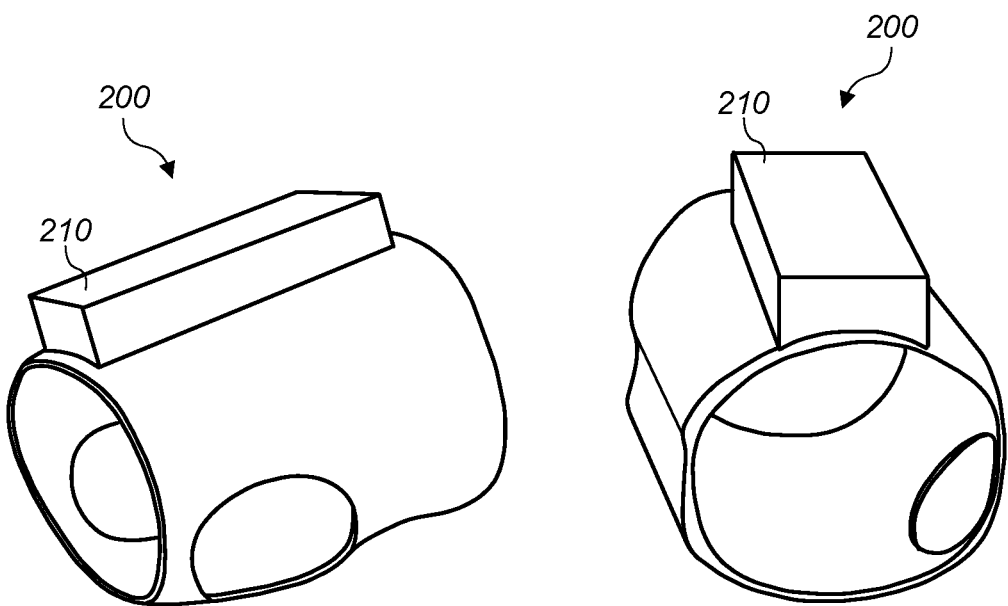
FIGS. 6A-6B depict a detachable jacket and a rectangular protection wall used for coupling a neural interface system to an animal.
Figure 7:
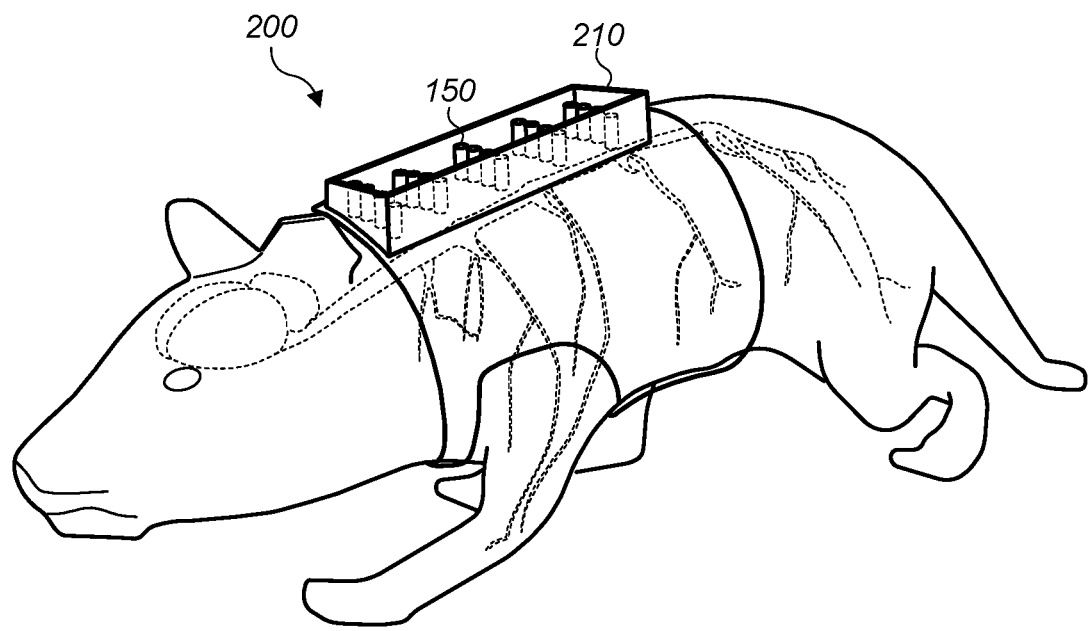
FIG. 7 depicts an animal with a jacket and a protection wall described in FIGS. 6A-6B.

FIGS. 6A-6B show a detachable jacket 200 and a protection container 210 used in the animal model. The container 210 protects from animal from biting and foot scratching the sockets 150 which could undermine the device's ability to remain intact. As the sockets are protruding from the animal's back, the chance that the animal will bite or damage them is high. FIG. 7 shows the animal with jacket 200 and a protection container 210. The animal wears a vest with a protection container 210 that surrounds sockets 150 on the animal's back. This shielding material is made out of solid materials as to prevent it from being chewed through, yet also maintains an ergonomic shape so the animal remains comfortable while wearing it.

Figure 9:
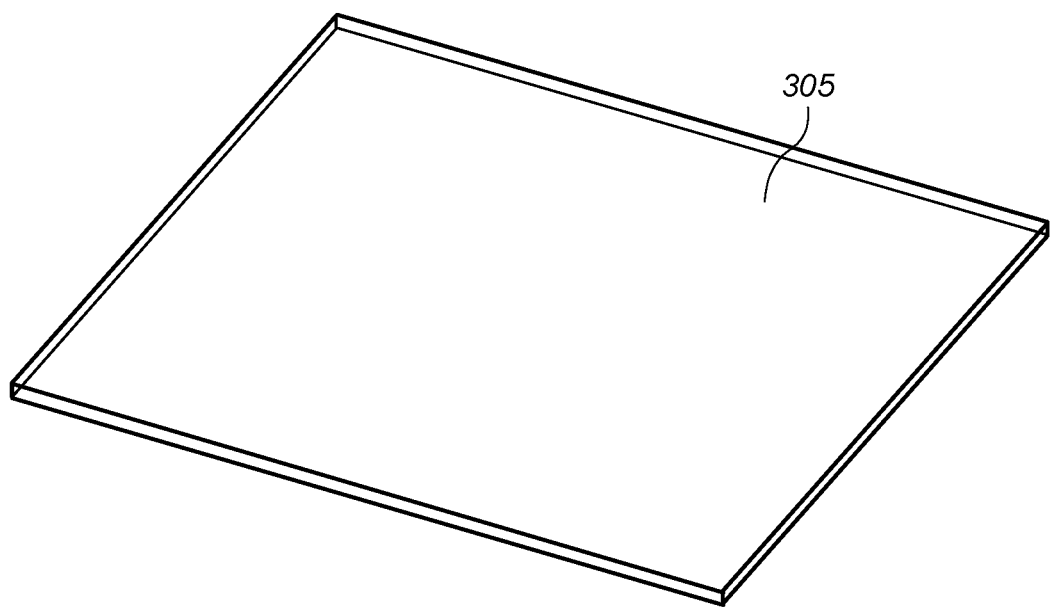
FIG. 9 depicts the intial step of a processing method for forming an INN device.

One form of locomotion testing involves placing the animal on a treadmill with all the connectors (both motor and sensory) linked to a neural signal monitoring system and computer analyzer. These signals can then be evaluated and analyzed by the end user (FIG. 9). The end user would also be able to stimulate individual connections via a feedback system which enables one to control a nerve response.

Figure 14:
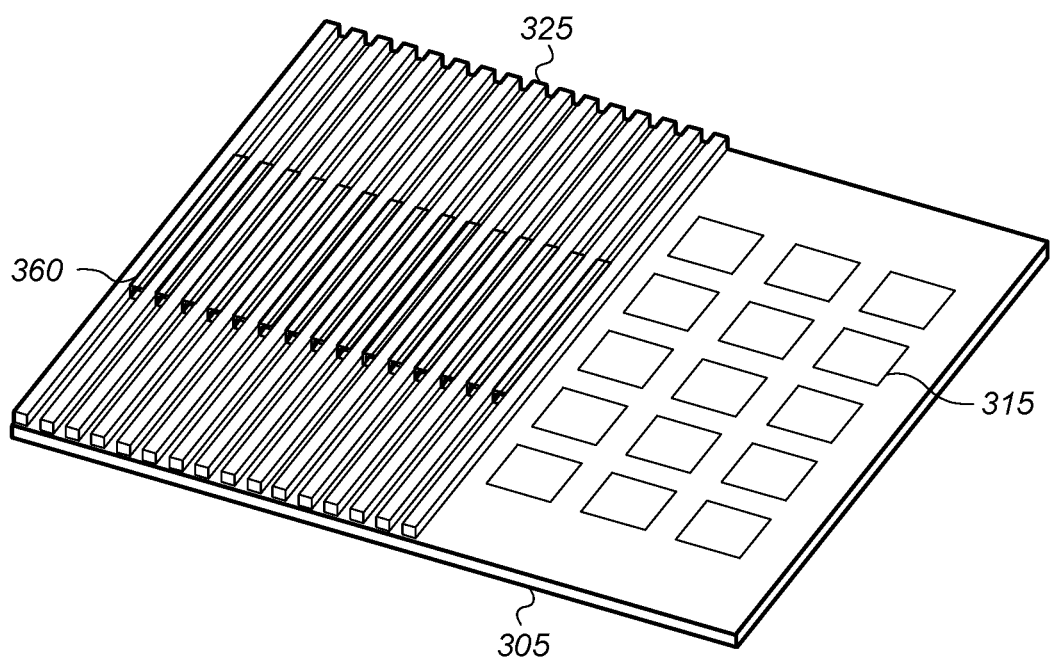
FIG. 14 depicts electrodes formed in microchannels.
Figure 15:
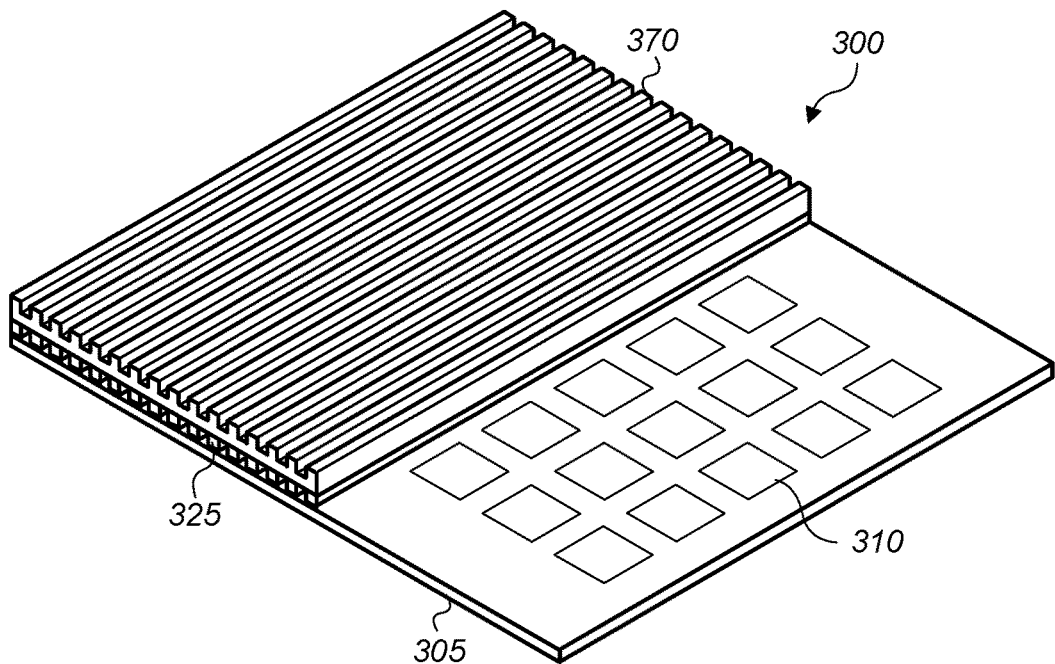
FIG. 15 depicts a second layer of microchannels formed on a first layer of microchannels.
Figure 16:
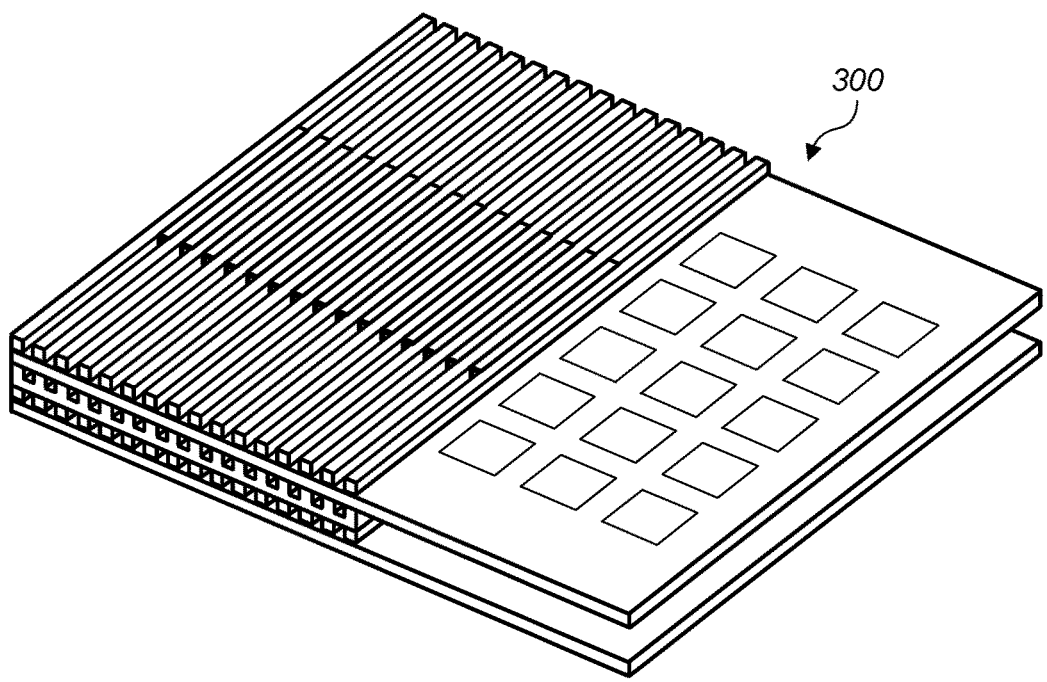
FIG. 16 depicts an INN device composed of stacked layers of microchannels.

An embodiment of an INN device 300 is depicted in FIG. 16. INN device 300 is composed of PDMS microchannels coupled to electrodes etched onto an inert substrate (e.g., a silicon wafer). FIGS. 9-15 depict the manufacturing steps used to create the INN device of FIG. 16.

In FIG. 9, an initial substrate is prepared by spin-coating a 10 to 1 mixture of Polydimethylsiloxane (PDMS, Sylgard 184®, Dow Corning, MI) and a curing agent on a silicon wafer. The PDMS mixture was degassed in a vacuum chamber and step cured starting at 70° C. for thirty minutes and then 90° C. for another thirty minutes. This forms a homogenous layer of PDMS on the silicon wafer.

Figure 10:
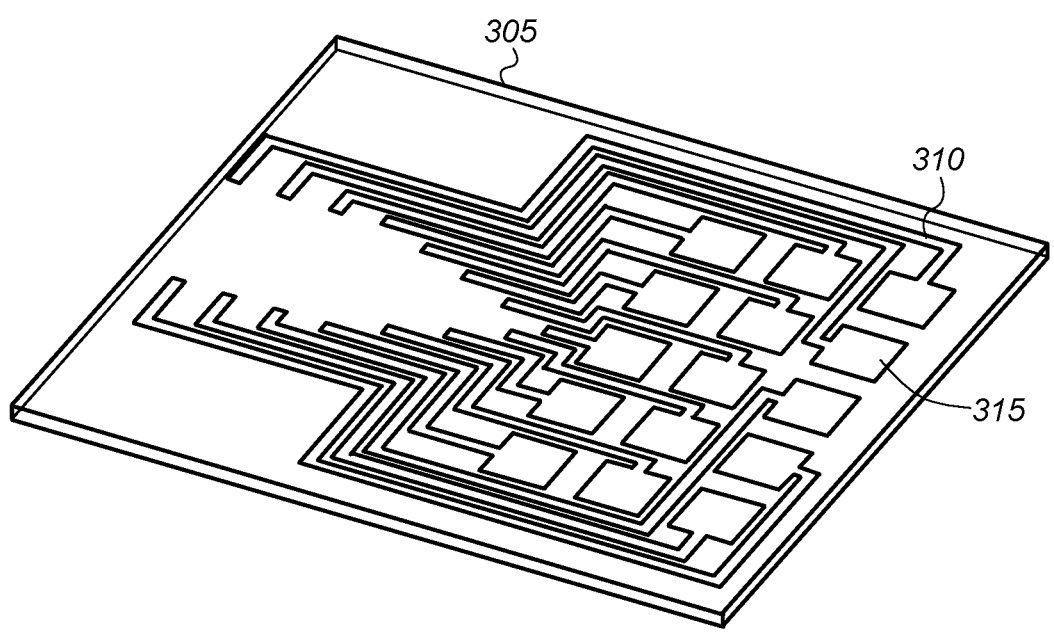
FIG. 10 depicts a substrate having electrode lines and contact pads.

In FIG. 10, electrode lines 310 and contact pads 315 formed from a conductive metal (e.g., gold) are formed on the PDMS layer using a lift-off process. In the lift-off process a photoresist (e.g., Futurrex NR9-8000) is placed on the PDMS layer and the photoresist is developed (UV exposure) so that the unexposed portions of the photoresist are positioned at the location of the electrode lines and contact pads. After UV exposure, the unexposed part of photoresist was removed by the developer leaving exposed substrate at the position of the electrode lines and contact pads. The conductive metal (e.g., gold) is deposited on the substrate to form the electrode lines and contact pads. Removal of the remaining photoresist material (e.g., by washing with an appropriate photoresist remover) leaves electrode lines and contact pads in the desired pattern on a PDMS substrate, as shown in FIG. 10.

Figure 11:
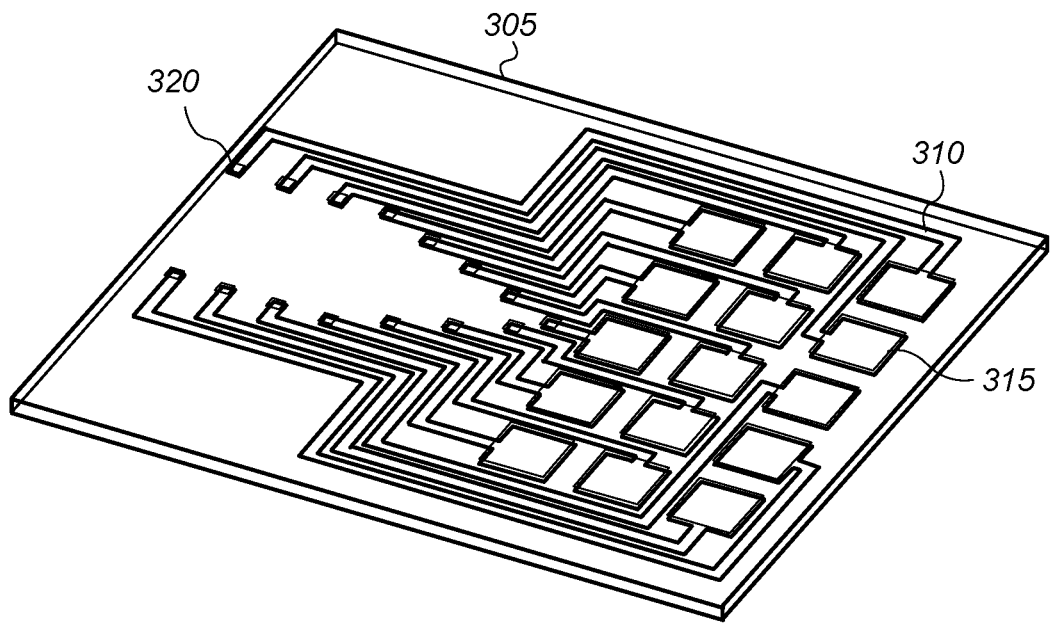
FIG. 11 depicts a substrate having defined contact pads and contact regions.

In FIG. 11 a second layer of PDMS is spin coated onto the gold electrode lines 310 and contact pads 315. A photolithographic process is used to define the contact pads 315 for electrical leads and to create contact regions 320 on each of the electrode lines. The photoresist is used as a mask to allow etching of the PDMS layer, forming the contact pads and contact regions through the second layer of PDMS.

Figure 12:
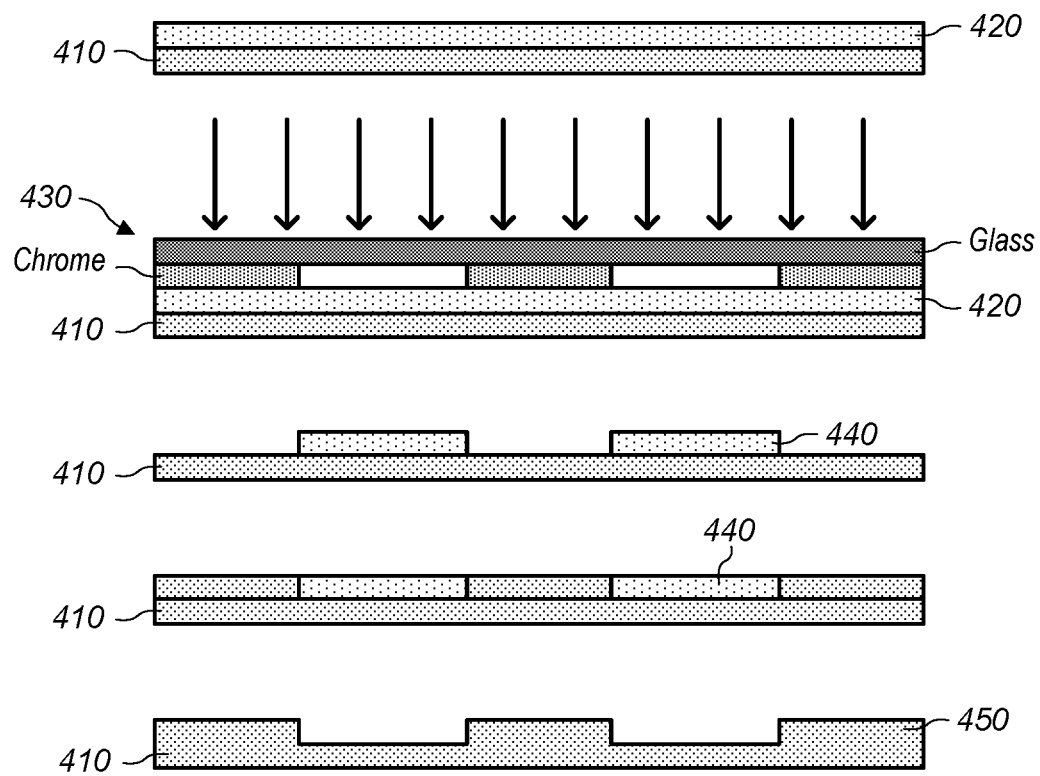
FIG. 12 depicts a processing scheme used to create microchannels.

FIG. 12 depicts a processing scheme used to create microchannels 325 (in this example, 15 microchannels) on the substrate. A photoresist layer 420 (e.g., NR9-8000) is applied to the second layer of PDMS 410 after etching of the contact pads and contact regions. The photoresist was patterned using mask 430 (e.g., a chrome coated glass mask) to cure the exposed portions of the photoresist. The uncured portions of photoresist are removed, leaving cured photoresist 440 to define the microchannels. The microchannels are defined such that a portion of the microchannel is aligned with at least one of the contact regions 320. The contact regions will be used to form an electrical connection between an electrode (described below) and the electrode lines.

Figure 13:
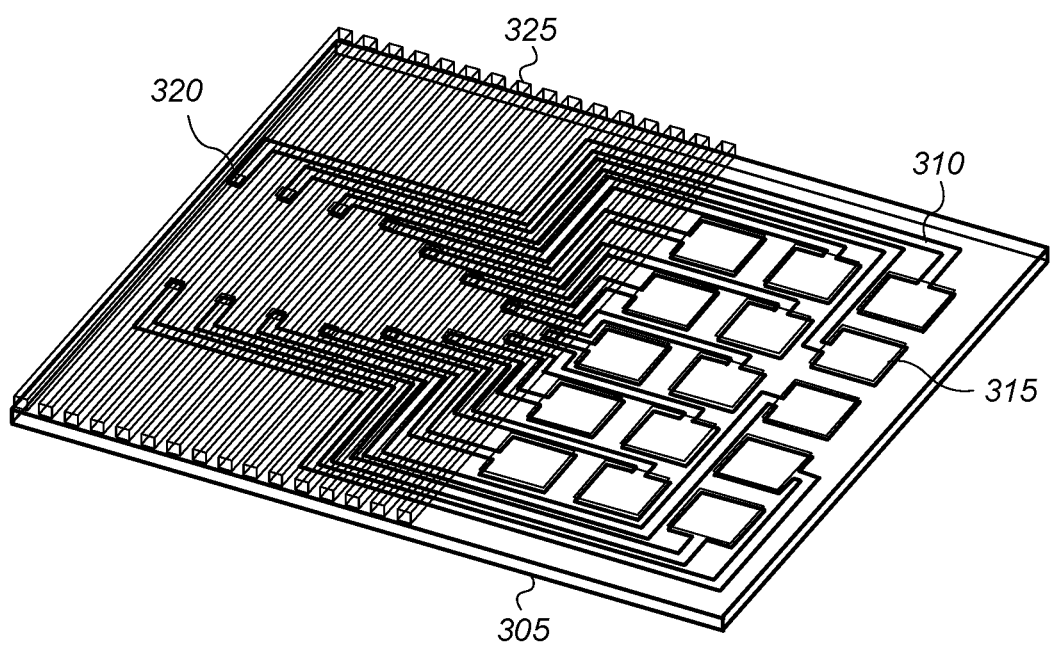
FIG. 13 depicts a microchannels formed in a substrate.

The cured photoresist 440 was used to define the microchannel sidewalls. PDMS was spin coated onto the substrate. Removal of photoresist 440 allows PDMS microchannel walls 450 to be formed by a lift-off process, where the photoresist removes the PDMS from the microchannel interior. FIG. 13 shows the second PDMS layer after the microchannel walls have been formed.

The microtube electrodes were fabricated by using a three-step photolithographic process. In which a bottom electrode layer is first formed, followed by the two microchannel wall contacts and then a top electrode layer to complete the tube structure.

In the first step a seed layer for metal electroplating is coated on the whole surface of the PDMS microchannels. A layer of photoresist (Futurrex NR9-8000) is spin-coated onto the microchannel layer, exposed, and developed to leave a portion of the bottom and side walls of the PDMS microchannels uncoated by photoresist. A gold metal layer is electroplated onto the uncoated microchannels, forming gold bottom and side wall contact. The gold bottom contact is also in contact with the contact regions 320 (not shown). The channel was then filled with copper using the photoresist to direct the copper in the microchannels. A third layer of gold was added to form a gold top layer in contact with the gold side walls previously formed. The photoresist was removed which allows access to the entire microchannel. The copper was removed using chemical etching to form the completed tube electrodes 360, as shown in FIG. 14.

In FIG. 15, a second insulating layer of PDMS microchannels 370 is stacked on top of the microtube electrode and the first layer of microchannels 325, thus sealing the microchannels. The second layer of microchannels is made using a process similar to the process used for the first layer of microchannels.

Several of these sections are then stacked atop each other to form the completed electrode with the required number of layers, as shown in FIG. 16.

Alternate Fabrication of Multilayer Microchannel Scaffold

Figure 17:
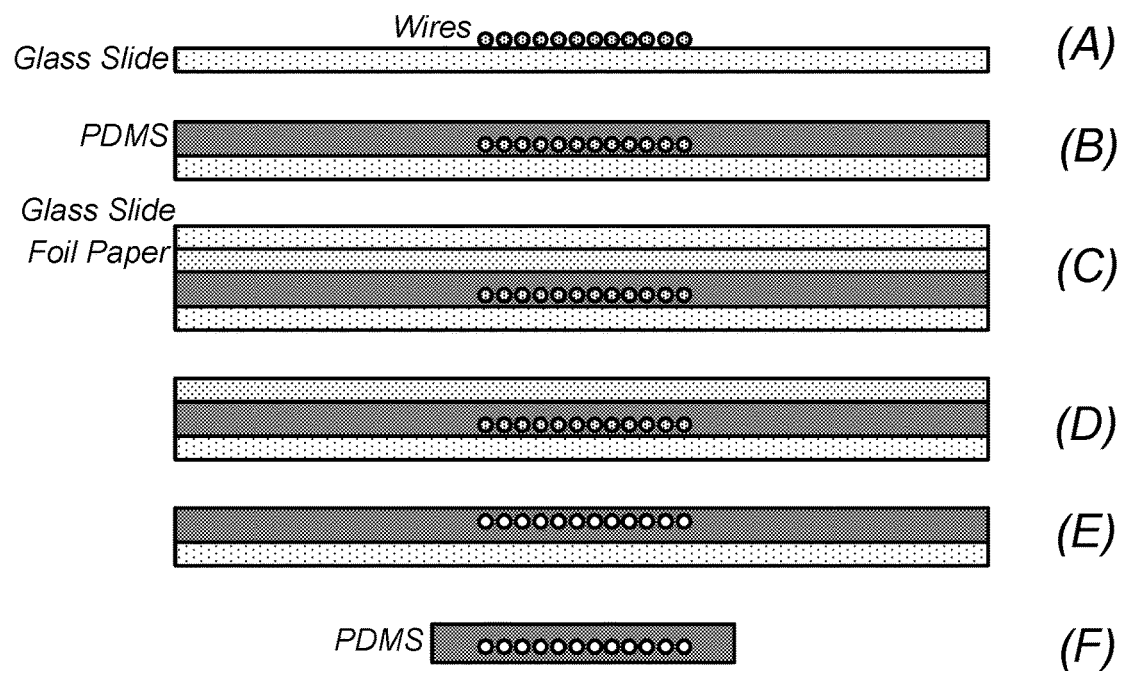
FIG. 17 depicts an alternate processing scheme for forming microchannels in a polymeric substrate.
Figure 18:
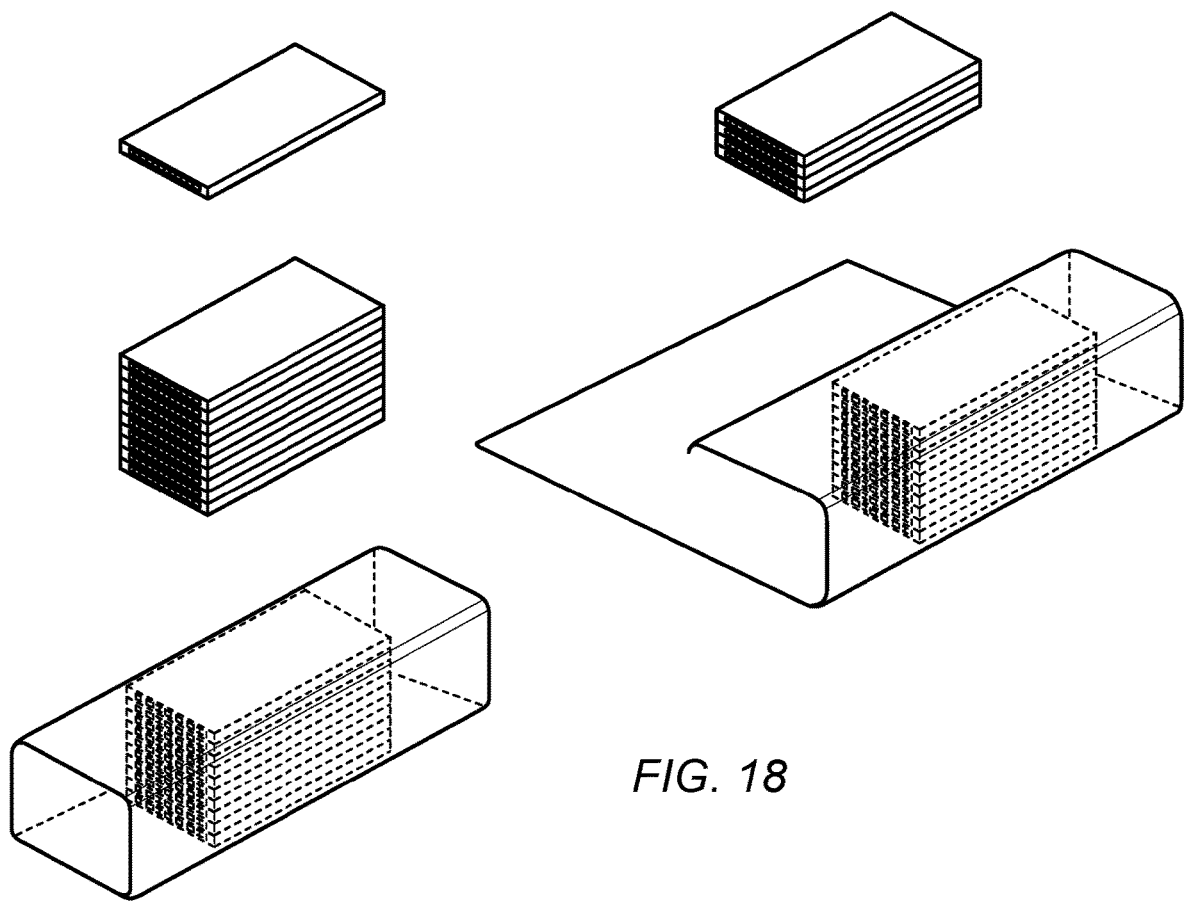
FIG. 18 depicts a scheme for the formation of an INN device by stacking a plurality of substrates having microchannels.

Another embodiment of an INN is depicted in FIGS. 17-18. The multilayer microchannels are made by the process schematically depicted in FIG. 17. No special micromachining equipment was required and commercially available microwires were efficiently used to implement the microchannel structures. The multilayer PDMS microchannel scaffold is composed of individual layers of microchannels manually fabricated by the steps shown in FIG. 17A-F. The individual microchannel layers were fabricated by first placing twelve 120 μm diameter microwires across a glass plate (FIG. 17A). PDMS was then poured across the wires, forming the mold for the channels within the layer, and then degassed in a vacuum chamber (FIG. 17B). Another glass plate with a thin aluminum foil covering was clamped PDMS side down to the channel mold to remove excess PDMS (FIG. 17C). This was then cured for two hours at 90° C. The aluminum foil allowed the top glass plate to be removed post curing without disturbing the cured PDMS microchannels (FIG. 17D). The aluminum layer was then carefully removed and the resultant sample was placed within a chloroform bath where the PDMS structure was swollen and the wires were removed longitudinally out from the PDMS structure (FIG. 17E). The PDMS structure was then submerged in isopropyl alcohol so that the sample would shrink to its original dimensions and remove any remaining chloroform. The microchannels at both ends (2 out of 12 microchannels) were used as guide lines to cut the microchannel scaffolds longitudinally. The guide lines were cut manually using the sharp tip of a X-Acto knife. Cutting both end channels of 12-channel structures left ten undamaged microchannels per layer.

The PDMS sample was then sliced into layers of the requisite size (e.g., 3 mm by 1.5 mm) (FIG. 17F) and stacked with a sufficient number of layers to form the required implant size (FIG. 18). This process allows a flexibility of sample size because the microchannels can be cut to any length from the initial length which only depends upon the size of the glass plate on which the PDMS and microwires are placed.

In order to disassemble individual PDMS layers after explant from nerve tissue, these layers were not secured together using an adhesive, but were wrapped with a PDMS thin film which was anchored to itself with a small portion of PDMS as shown in FIG. 18. The stacked microchannel layers could be extracted and separated after nerve regeneration without sample damage. Microchannel layers of approximately 3 mm long and 1.5 mm wide were stacked to reach a height of approximately 1.5 mm, corresponding to the dimensions of a rat's sciatic nerve. Eight devices were fabricated and implanted in the sciatic nerves of eight Lewis rats.

Implantation of Multilayer Microchannel Scaffolds

Figure 19:
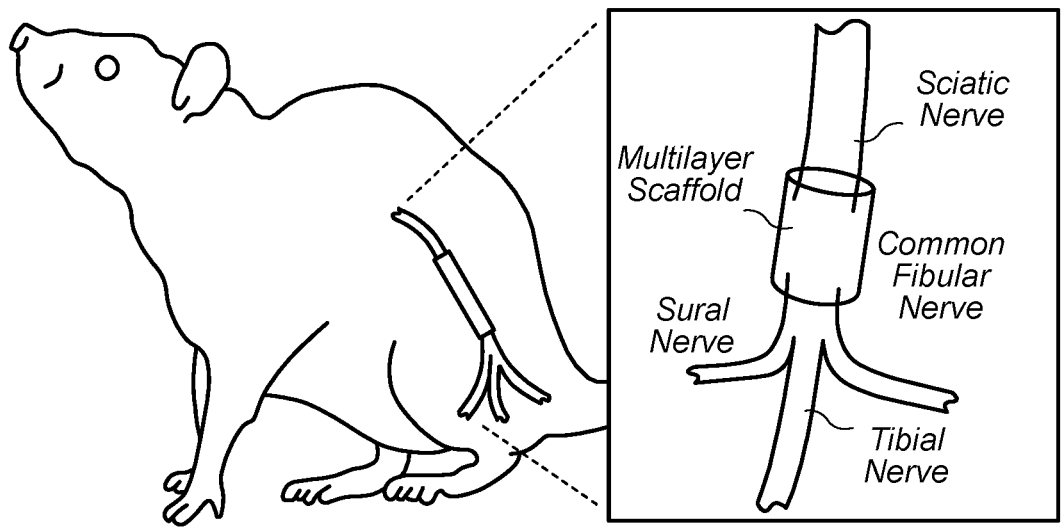
FIG. 19 depicts a schematic diagram of the implantation site.

Surgical procedures were performed under aseptic conditions at the UTPA Animal Facility. Prior to implantation, a Lewis rat was placed into an induction chamber and subjected to gas anesthesia (5% Isoflurane with oxygen) until unconscious. The surgery location (right thigh) was shaved and cleaned using a betadine scrub and isopropyl alcohol. Its maxillary central incisors were hooked into a gas mask through which it continued to receive small doses of anesthesia (2% Isoflurane). It was secured to a surgery table and its body temperature was regulated with the placement of a heat pad. Incisions were made along the right thigh to expose the sciatic nerve. The nerve was severed, proximal to the tibial and fibular nerves, and the multilayer microchannel scaffold was implanted by suturing both the distal and proximal ends of the nerves to the guides of the device. FIG. 19 depicts a schematic diagram of the implantation site. All procedures conformed to the Guide for the Care and Use of Laboratory Animals of the Institute of Laboratory Animal Resources, Commission on Life Sciences, National Research Council. They were reviewed and approved by the Institutional Animal Care and Use Committee UTPA.

At two different times after device implantation, two and four weeks (four rats per condition, total eight rats), animals were euthanized and perfused transcardially with saline followed by 4% paraformaldehyde in 1×PBS. The integrity of the regenerated sciatic nerve was examined and post-fixed for 24 hours in 4% paraformaldehyde (Sigma-Aldrich). The samples were rinsed again in 1×PBS and transferred to 30% sucrose solution in phosphate buffer, pH 7.4, for cryoprotection. White colored regenerated nerve and the microchannel scaffold are observed together in the samples. The samples were then embedded in O.C.T. gel (Tissue Tek) and stored at −80° C. until the time of cryosectioning. A cryostat (CM1850, Leica) was used to collect cross-sectional nerve tissues from proximal side. When it reached the end of the microchannel scaffold, cryosectioning was stopped. OCT around the sample was melted down to extract the microchannel scaffold. Individual layers can be separated as no adhesive was used between the layers. The diameter of both distal and proximal nerve stumps was found to be slightly smaller than the diameter of microchannel scaffolds. However the regenerated nerves covered the whole cross section of the microchannel scaffolds and the regenerated nerves were observed throughout all microchannels during the evaluation process.

Histology

Because cryosectioning was used to harvest the edge of the multilayer structures, general IHC protocol for frozen sections was performed. Sections were later reacted for immunofluorescent demonstration of a marker on axons, neurofilament 160 targeted by a primary antibody (NF160, 1:250 dilution, Sigma-Aldrich). Nuclei were labelled with DAPI (Invitrogen). Goat anti-mouse IgG1 Alexa 488 was used as a secondary antibody. IHC procedure was started by thawing and cleaning the frozen tissue sections using 1×PBS. Then tissue sections were incubated for one hour at room temperature in a blocking solution of 4% goat serum (Invitrogen) in 1×PBS containing 0.5% Triton X-100 (Sigma-Aldrich). Sections were then incubated overnight at 4° C. in a mixture of primary antibody and blocking solution, then washed and incubated for 1 hour at room temperature in a solution of secondary antibody, diluted 1:220 in 0.5% Triton in PBS. Finally, the sections were washed once more and dried. Mounting media (Fluoromount-G™ with DAPI, eBioscience) was applied on the tissue and cover-slipped for evaluation.

3D renderings of the microchannels within a scaffold layer were obtained by digitally portioning the entire microchannel nerve section into rectangular nerve blocks and then obtaining a Z-stack image using an Olympus FV10i confocal microscope, and rendered using FV10-ASW data acquisition software.

IHC analysis (individual layer stained with NF160) revealed that the microchannel scaffolds facilitated the robust nerve regeneration of transected sciatic nerves. All 80 microchannels were occupied by regenerated nerves. Regenerated nerves in four-week nerve regeneration show more axons comparing to two-week nerve regeneration. The obtained data from individual microchannels and the axonal growth patterns from 3D confocal imaging show the details of the regenerated axonal growth, such as individual growth cones and axon branching, which were not observable using conventional methods. Viewing the rendered regenerated nerves at various angles demonstrates the distribution of axons throughout the regenerated nerves.

Though the initial IHC analysis supports the assertion that this particular scaffold structure does facilitate axon growth, more thorough analysis of individual axon morphologies were made available from the confocal images. These images provide clear examples of individual axon growth, as well as allowed the observation of general axon growth within the constricted, 3 mm length scaffold channels. The numbers of axons were counted by scanning the 3D confocal images. Observation of the z-stack images of layer sections post removal after the second week showed an average of 15 axons per 120 µm diameter channel out of four animals per group.

After two-weeks, regenerated nerves contained both significant number of growth cones and several nerve splitting aspects. Though some motor and sensory axon types are indistinguishable by size alone, some sensory axon types are considerably thinner than most motor axons, and therefore these size characteristics may be of use for identifying axon modality. Taking the relative thickness and branching behavior of the largest axon seen in comparison to its nearest neighbor, it can be inferred that the large branching axon is probably a motor type while the thinner axon close next to it within the frame is probably a sensory type.

Figure 20A:
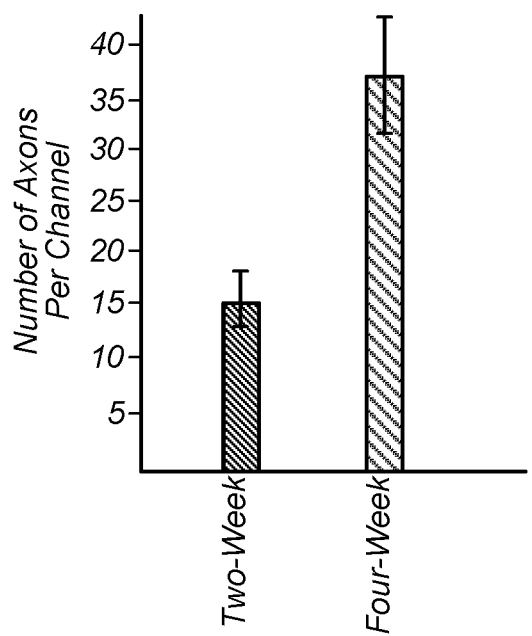
FIG. 20A shows the population of the regenerated axons averaged per 120 µm diameter microchannel.
Figure 20B:
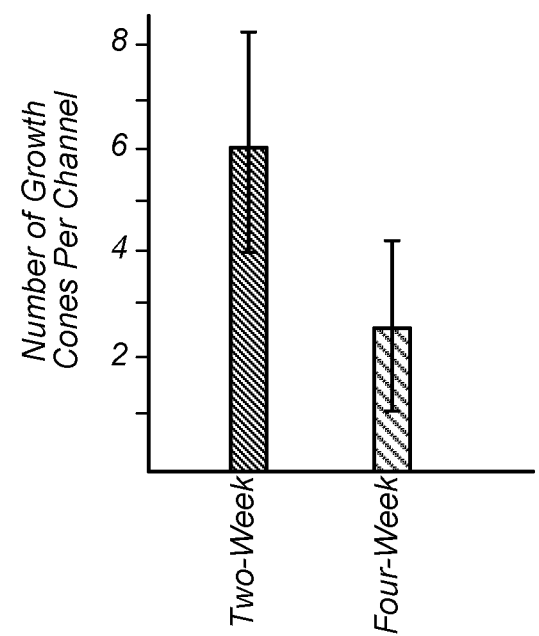
FIG. 20B shows the number of growth cones (FIG. 20B) averaged per 120 µm diameter microchannel.

The appearance of growth cones and axon branching suggested that the initial nerve regeneration process had been performed actively during the first two weeks in order to support and facilitate an axon growth population of the size observed. The z-stack images of the samples extracted the fourth week post implantation showed individual channels that appeared to have reached their axon population limits, 38 axons on average in a 120 µm diameter out of four animals per group, based on the decreased observation of growth cones. It was conjectured that reduced axon growth was due to space limitation within the channels. FIG. 20 shows the population of the regenerated axons (FIG. 20A) and the number of growth cones (FIG. 20B) averaged per 120 µm diameter microchannel.

Discussion

Since the configuration of the multilayer microchannel scaffold can be easily modified in the fabrication process, scaffolds for use in a variety of nerve gap injuries can be quickly fabricated on an individual case basis with a minimum of expense. Scaffold design changes would merely require an increased or decreased number of channels per layer of scaffold width, a variable number of layers for scaffold height, and in the case of diameter control, simply a variety of microwires for the microchannel molds.

A plethora of nerve regeneration scaffolds have been introduced over the last few decades, ranging from empty tube conduits to porous or microfiber scaffolds with varying degrees of success. While porous/fiber scaffolds, including some that mimic the physical characteristics of the extracellular matrix or are developed from nerve allografts, have relatively small diameter paths, allowing for a more even distribution of and physical support to axon growth from the proximal to the distal stump, and therefore a decreased chance of either functional mismatch in comparison to tube conduits and larger diameter channel array scaffolds, they do not provide much in the way of directionality. Decreasing channel diameters and increasing channel density may provide similar axon distribution and physical support while increasing axon growth directionality and axon separation and eventually axon selectivity.

As a further advantage of the axon separation, the multilayer microchannel scaffold may also be used as a base structure for neural interfaces, because constricting regenerated axons in a microchannel increases the signal quality of the action potential signal. Neural signal recording in vivo is often corrupted by a great number of noise sources, especially from muscle cell action potential signals. When the axons are insulated in a constricted microchannel, constricting extracellular space, the range of relevant recordable voltage amplitudes will be significantly increased and therefore cleaner signal recording becomes possible.

For both nerve regeneration observation and neural interface applications of this scaffold, permanent implants are a necessity for the future translational approach. The demonstrated fabrication process of multilayer scaffolds could also be adapted for biodegradable polymers. The unique microwire molding technique could be easily combined with high temperature polymer melting and reforming methods.

Multilayer microchannel scaffolds could be invaluable in future analyzing tools, if they are combined with biochemical cues to separate the growth of modality specific axons into individual microchannels. Inducing the growth from a single tube structure to biochemically infused microchannels could provide data for a more in-depth analysis of axon growth behavior. In the future, this device may be used in conjunction with electrode arrays and signal processing techniques for prosthetic control applications or be fabricated from biodegradable polymers for solely nerve regeneration purposes.

CONCLUSIONS

Multilayer microchannel scaffolds were developed and successfully implanted within the sciatic nerve of eight Lewis rats and harvested post implantation to give detailed information regarding the nerve regeneration process. Multilayer microchannel scaffolds increased the amount and quality of the data extracted from each animal due to the increased numbers of longitudinal tissue samples through all individual layers and microchannels of each layer. Multilayer microchannel scaffolds in combination with IHC and confocal microscopy allowed the limited identification of axon types and growth patterns of peripheral nerve regeneration in three dimensional detail, including examples of both growth cones and axon branching.

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of making a microchannel neural interface device comprising:
    placing a plurality of metal wires in a curable composition, wherein the curable composition comprises a polymerizable compound and wherein the metal wires have a diameter approximately equal to the diameter of a nerve axon;
    curing the curable composition to form a polymeric object having a plurality of metal wires embedded in the polymeric object;
    removing the metal wires from the polymeric object to form a plurality of microchannels within the polymeric object; and
    placing one or more hollow cylindrical electrodes into one or more of the microchannels, wherein each of the one or more hollow cylindrical electrodes is an elongated electrode with a hollow part of the electrode oriented coaxially with the longitudinal axis of the microchannels.

2. The method of claim 1, wherein the metal wires are copper wires.

3. The method of claim 1, wherein the curable composition comprises a curable monomer.

4. The method of claim 3, wherein the curable monomer is a monomer capable of being polymerized into polydimethylsiloxane.

5. The method of claim 1, wherein removing the metal wires comprises dissolving the metal wires.

6. The method of claim 1, wherein the hollow part of the electrode extends along a length of the electrode.

7. The method of claim 1, wherein the one or more hollow cylindrical electrodes are microtube electrodes.

8. The method of claim 1, wherein the one or more hollow cylindrical electrodes are designed to allow neural recording and stimulation signals to flow longitudinally within hollow parts of the electrodes.

* * * * *